United States Patent [19]

Schwarz et al.

[11] Patent Number: 5,254,532
[45] Date of Patent: * Oct. 19, 1993

[54] PREPARATION FOR TREATING AND PREVENTING THROMBOSES AND THROMBOEMBOLIC COMPLICATIONS, USE OF SUCH A PREPARATION AND A METHOD OF PRODUCING THE SAME

[75] Inventors: Hans P. Schwarz, Vienna; Ewald Molinari, Modling; Yendra Linnau; Susanne Pfeiler, both of Vienna, all of Austria

[73] Assignee: Immuno Aktiengesellschaft fur chemisch-medizinische Produkte, Vienna, Australia

[ * ] Notice: The portion of the term of this patent subsequent to Sep. 1, 2009 has been disclaimed.

[21] Appl. No.: 840,719

[22] Filed: Feb. 21, 1992

Related U.S. Application Data

[63] Continuation of Ser. No. 540,357, Jun. 19, 1990, Pat. No. 5,143,901.

[30] Foreign Application Priority Data

Jun. 26, 1989 [AT] Austria .................................. 1551/89

[51] Int. Cl.$^5$ ............................................. A61K 37/00
[52] U.S. Cl. ........................................... 514/2; 514/8; 514/12; 514/24
[58] Field of Search ........................... 514/2, 8, 12, 21

[56] References Cited

FOREIGN PATENT DOCUMENTS 0255771 2/1988 European Pat. Off. .
0286323 10/1988 European Pat. Off. .

OTHER PUBLICATIONS

English language abstract of PCT Patent Application No. WO 8902747 (Apr. 6, 1989).
English language abstract of European Patent Application No. EP 255771 (Feb. 10,1988).
Jenny R. et al., "Purification of six human vitamin K-dependent proteins in a single chromatographic step using immunoaffinity columns." Prep. Biochem. 16(3), 1986, 227-246. [Biological abstract No. 82108551 only].
Litwiller R. D. et al., "Monoclonal antibodies in human vitamin K-dependent protein S." Blood 67(6) 1986, 1583-1590 [Biological abstract No. 82050635 only].
Kohler and Milstein, "Continuous Cultures of Fused Cells Secreting Antibody of Predefined Specificity", Nature, 256:495-497 (1975).
Schwarz et al., "Plasma Protein S Deficiency in Familial Thrombotic Disease", Blood, 64:1297-1300 (1984).
Griffin et al., "Plasma Protein S Deficiency and Thromboembolic Disease", Progress in Hematology, 15:39-49 (1987).
Laurell, "Electroimmuno Assay", Scand. J. Clin. Lab. Invest., 29:21-37 (1972).
Lowry et al., "Protein Measurement With the Folin Phenol Reagent", J. Biol. Chem., 193:265-275 (1951).
Laemmli, "Cleavage of Structural Proteins During the Assembly of the Head of Bacteriophase T4", Nature, 227:680-685 (1970).
Fareed et al., "A Modified Stasis Thrombosis Model to Study the Antithrombotic Actions of Heparin and its Fractions", In: Seminars in Thrombosis and Hemostasis, II:155-175 (1985).
Wessler et al., "Biological Assay of a Thrombosis-Inducing Activity in Human Serum", J. Appl. Physiol., 14:943-946 (1959).
Comp et al., "Familial Protein S Deficiency is Associated with Recurrent Thrombosis", J. Clin. Invest., 74:2082-2088 (1984).

Primary Examiner—S. J. Friedman
Attorney, Agent, or Firm—Brumbaugh, Graves, Donohue & Raymond

[57] ABSTRACT

A preparation for the treatment and prevention of thromboses and thromboembolic complications is disclosed, which preparation has a content of protein S at a concentration at least 50 times that present in native plasma and is free from C4b-binding protein, optionally in combination with a content of activated protein C.

7 Claims, No Drawings

PREPARATION FOR TREATING AND PREVENTING THROMBOSES AND THROMBOEMBOLIC COMPLICATIONS, USE OF SUCH A PREPARATION AND A METHOD OF PRODUCING THE SAME

This application is a continuation of application Ser. No. 07/540,357, filed on Jun. 19, 1990, now U.S. Pat. No. 5,143,901.

The invention relates to a protein-S-containing pharmaceutical preparation having antithrombotic activity as well as to the use of purified protein S for producing preparations having antithrombotic activity.

Antithrombotic substances presently available involve the risk of haemorrhages as a side effect. Thus their application in clinical situations associated with an increased risk to thromboses involves considerable side effects.

Protein S is a physiologically occurring antithrombotic substance which inhibits clotting and simultaneously exhibits pro-fibrinolytic properties. Native plasma contains between 25 μg and 30 μg of protein S per milliliter. Protein S is a non-enzymatic co-factor for the anticoagulating and pro-fibrinolytic properties of activated protein C. Activated protein C accelerates the inactivation rates of both activated factor V and activated factor VIII.

From printed publications (Blood, Vol. 64, No. 6 (December), 1984, pages 1297 to 1300, as well as Progress in Hematology, Vol. XV, ISBN 0-8089-1861-3 (1987), pages 39 to 49) it is furthermore known that protein S is a vitamin K-dependent protein synthesized in the liver, in the endothelium and in megakaryocytes. According to its structure protein S is a single-chain glycoprotein having a molecular weight of approximately 70,000. It consists of 635 amino acids. In the plasma, protein S is present in various forms; i.e., in the free, active form to a slighter extent, and as a non-covalent complex with C4b-binding protein—which complex is inactive—to a larger extent, approximately 60%.

Activated protein C increases the plasma clotting time in a dose-dependent manner. In a protein S-immunodepleted plasma, activated protein C cannot develop its function. Activated protein C will become fully effective again only after reconstituting a protein S-deficient plasma with purified protein S. Its pathophysiological role becomes apparent from the description of individuals suffering from a congenital protein S deficiency and thrombophilia. A congenital protein S deficiency is autosomal-dominantly inherited and is characterized by the occurrence of venous and arterial thromboembolisms in early youth.

The invention has as its object to provide a therapeutically usable protein S-containing preparation, which, due to a specific purification procedure, has a concentration that is higher by a multiple than the protein S concentration in native plasma and is free from components reducing its effect.

To obtain this object, the invention provides preparation for treating and preventing thromboses and thromboembolic complications, having a protein S content in a concentration that is at least 50 times that of native plasma and being free from C4b-binding protein optionally in combination with a content of activates protein C.

The protein S concentration purified and highly concentrated according to the invention by specific purification and concentration procedures may advantageously be used for producing various therapeutic compositions.

One proposal for a utilization according to the invention relates to the use of protein S purified by polyclonal affinity chromatography or by monoclonal anti-protein S affinity chromatography for the production of therapeutic preparations for the prevention of thromboembolic complications in patients afflicted with congenital or acquired protein S deficiency conditions.

A further utilization proposal regards the use of protein S purified by polyclonal affinity chromatography or by monoclonal anti-protein S affinity chromatography for the production of therapeutic preparations for the treatment of patients suffering from conditions involving an increased level the C4b-binding protein.

A further preferred utilization proposal is the use of protein S purified by polyclonal affinity chromatography or by monoclonal anti-protein S affinity chromatography, optionally in combination with activated protein C-for the production of preparations capable of being immobilized at the surfaces of artificial vessels to prevent thrombosing.

The production, purification, and evaluation of preparations according to the invention will be explained in more detail in the following examples.

EXAMPLE 1

Purification of protein S from a prothrombin-complex concentrate

Human protein S was prepared from a factor IX concentrate (prothrombin complex STIM-3 IMMUNO AG Vienna) by means of QAE-Sephadex and Blue Sepharose CL-6B chromatography (Pharmacia) in the following manner:

The lyophilized concentrate (100 g) was dissolved in 200 ml of sterile ion-free water and dialized against a buffer comprised of 0.01 mol/l 2-(N-morpholine ethane sulphonic acid), pH 6.0; 0.18 mol/l NaCl, 10 mmol/l EDTA, 2 mmol/l benzamidine-HCl and 0.02% NaN$_3$ (starting buffer). The dialyzed material was then applied to a QAE-Sephadex column (8×19 cm) and equilibrated with the above-mentioned buffer. As the washing solution, 1.5 l of buffer (starting buffer) were used.

Protein S was eluted with 110 ml/h with a linear NaCl gradient comprised of 1.2 l of starting buffer and 1.2 l of a further buffer, differing from the first buffer by the addition of 0.5 mol/l NaCl. The protein S fraction was examined for protein S by mens of Fast Flow SDS Page (Pharmacia) and antigen determination (Laurell), and protein S-containing fractions were pooled and finally dialyzed against a buffer. This buffer contained 50 mmol/l Tris-HCl, pH 7.4, 150 mmol/l NaCl, 2 mmol/l EDTA, 1 mmol/l benzamidine-HCl and 0.2% NaN$_3$. After the dialysis the protein S pool was applied to a Blue Sepharose column CL-6B (2.5 cm×10.5 cm) and equilibrated with the starting buffer.

Washing was effected at a rate of 15 ml/h with 500 ml of starting buffer. Thus protein S could be eluted in the "void volume", while prothrombin adsorbed on the column. The fractions rich in protein S were again determined by means of SDS-Page Fast Flow System (Pharmacia and Laurell) (Scand. J. Clin. Invest. (Suppl.)29(1977)21(Suppl.124)).

At a reduced SDS-Page the protein S thus produced exhibited the morphology characteristic of protein S, i.e., two close bands (doublet) having a molecular weight of approximately 86,000 and 76,000, respectively. The protein concentration was spectrophotometrically determined with the help of an extinction coefficient of 0.1 at 280 nm for human protein S and was verified by the method of LOWRY (Lowry O., Rosebrough N., Farr A. L., Randall R., Protein measurement with the Folin phenol reagent, J. Biol. Chem. 193 (1951)265).

EXAMPLE 2

Immunization of sheep with protein S

Pre-purified protein S prepared according to Example 1 was used for the preparation of sheep-antiserum to protein S by making four immunising injections, wherein in the first two injections 100 μg of protein S with Freund's adjuvant were subcutaneously applied and in the following boosts were with incomplete adjuvant. After further boosts the antiserum was tested by double immunodiffusion. It showed precipitation with purified protein S and with normal plasma.

EXAMPLE 3

Purification of protein S by means of polyclonal affinity chromatography

The IgG fraction from 450 ml of antiserum was obtained by alcohol precipitation and subsequent adsorption on Sephadex A 50 in Tris-HCl buffer, pH 6.8. From 450 ml of antiserum, the supernatant contained 1.14 g of anti-protein S IgG. The IgG fraction was coupled to 450 ml of Sepharose CL-4B, wherein 5.7 mg of protein were used per ml of Sepharose. The coupling efficiency was 76%. The anti-protein S column was equilibrated with glycine-HCl, pH 3, and absorption buffer, pH 7.5.

The absorption buffer was comprised of 20 mmol Tris, 2 mmol EDTA, 0.25 mol NaCl, 2 mmol benzamidine, 0.02% Tween 20 and 0.02% NaN$_3$, pH 7.4. The washing buffer solution had the following contents: 20 mmol Tris, 2 mmol EDTA, 1.0 mol NaCl, 0.5 mmol benzamidine, 0.01% Tween 20; 0.02% NaN$_3$, pH 7.4.

The eluting buffer had the same composition as the washing buffer solution, with the alteration that 0.05% Tween 20 and an additional 243.3 g of NaSCN, pH 7.4 (a 3 mol rhodanide solution) were used.

The dialysis buffer solution contained 20 mmol Tris, 0.15 mmol glycine, 1 mmol EDTA, 2 mmol benzamidine, pH 8.3.

For a further purification according to the invention, 100 g of the protein S fraction produced from prothrombin complex concentrate according to Example 1 were dissolved in 1 l of absorption buffer and dialyzed against an absorption buffer solution overnight. After the sample had been applied, the column was washed free from protein with washing buffer, about 5 l, and subsequently elution was effected with 3 mol NaSCN in the elution buffer solution. The eluate was dialyzed immediately until SCN was below the detection limit; the eluate had a concentration of 500 μg/ml protein S. It was free from C4b-binding protein.

EXAMPLE 4

Purification of protein S by means of monoclonal anti-protein S affinity chromatography Monoclonal anti-protein S antibodies were prepared as follows:

BALB/C mice were immunized with 100 μg of the protein S prepared according to Example 1 at two-week intervals of intraperitoneal injection. After six weeks 50 μg of human protein S were once again injected, and three days later fusion was effected. The myeloma cell line (P3-X-63-AG 653, $1.5 \times 10^7$ cells) was mixed with $1.7 \times 10^8$ spleen cells from a mouse, and fusion was effected according to the modified Köhler & Milstein method by using PEG 1500 (Köhler G., Milstein C., Nature 256 (1975) 495–497).

Positive clones, tested by ELISA, were twice subcloned. Ascites production was effected by injecting $5 \times 10^6$ hybridoma cells per BALB/C mouse two weeks after pristane treatment.

The immunoglobulin was recovered from ascites by ammonium sulphate precipitation and purified by subsequent chromatography by means of QAE Sephadex followed by chromatography on Sephadex G200.

The IgG fraction recovered from ascites and prepurified from protein A Sepharose was coupled to Sepharose CL-4B. The purification of protein S by affinity chromatography, which protein S was recovered from prothrombin complex concentrate according to Example 1, was carried out under the conditions set forth in Example 3 for polyclonal protein S antibodies. The protein S concentration of the eluate was 600 μg/ml. It was free from C4b-binding protein.

The protein S preparations that were highly purified according to the method of the polyclonal or the monoclonal affinity chromatography were subjected to an SDS Page (gradient gel 8 to 12%), and, by the aid of Coomassie staining (Laemmli U.K.: Cleavage of structural proteins during the assembly of the head of bacteriophage T4, Nature 227 (1970) 680) they can be said to be more than 95% pure.

EXAMPLE 5

The protein S eluates prepared according to Examples 3 or 4 were completed in the following manner to give pharmaceutically applicable preparations:

At first, the eluates were subjected to an ultrafiltration and a diafiltration step. For diafiltration, a buffer having a pH of 7.4 was used, which contained 150 mmol NaCl and 15 mmol trisodium citrate.2H$_2$O per liter. The filtrates obtained were freeze-dried and virus-inactivated (for removing any viral contaminations of polyclonal or monoclonal antibody possibly present) by a one hour vapour treatment at 80° C.±5° C. and 1375 ±35 mbar.

The lyophilized virus-inactivated material was then dissolved in a sterile isotonic NaCl solution and any antibodies or serum amyloid P possibly present were removed by ion exchange chromatography on Q-Sepharose. The purified solution was concentrated by a further ultrafiltration and a diafiltration step. Thereafter 10 g of albumin, 150 mmol of NaCl and 15 mmol of trisodium citrate were added per liter of the solution obtained. The pH of the solution was 7.5. It contained 3000 μg/ml of protein S. This protein S content corresponds to a 500-fold enrichment as compared to plasma. Mouse immunoglobulin as well as the factors II, VII, IX and X could not be detected. Then the solution was sterile-filtered, filled in containers and lyophilized.

The effect of the preparations in preventing thromboses is expressed in the following thrombosis model:

White male New Zealand rabbits weighing from 2.5 to 3 kg were used for this test. The animals received an anesthesia consisting of urethane (50% solution) at a dose of 2 g/kg body weight.

After having been anaesthesized, the animals were placed in a retaining arrangement in the supine position. After shaving of the front area of the neck, a longitudinal incision was made to prepare the jugular veins on both sides for approximately 3 cm. 50 s before ligature, 25 units per kg of FEIBA (=thrombogenic substance, thrombus stimulus) were injected into the contralateral ear vein. The ligature was maintained for 10 or 20 min respectively. Subsequently the vein was removed, and after opening of the vessel the thrombus that had formed was visually graded on a scale of from 0 to 4, "0" indicating the absence of a clot and "4" indicating a hard clot, free from exudate.

This model has been described in the literature (Seminars in Thrombosis and Hemostasis 11 (1985) 155; J. Appl. Physiol. 14 (1959) 943–946) for evaluating antithrombotic substances.

In the present test series, protein S was applied in various doses via the ear vein, 5 min before the FEIBA injection. Protein S was rated to be effective for thrombosis prevention if the clot was graded +1 or less.

Protein S injected in doses of from 0.5 to 1.2 mg/kg 5 min prior to FEIBA application (25 U/kg) was effective in 11 animals. At a 20 minute stasis, protein S was effective in doses of more than 1.5 mg (3 animals). The maximum volume used was 7 ml. Controls consisting of protein S-buffer used in 7 and 10 ml had no thrombosis-preventing effect.

As has already been mentioned, a preferred embodiment of the invention is the use of a combination of protein S purified according to the invention and activated protein C.

EXAMPLE 6

Preparation of activated protein C

Highly purified activated protein C was prepared analogous to the procedure described in Example 4 for protein S, by initially preparing a crude protein C fraction from commercially available prothrombin complex concentrate. Monoclonal antibodies for protein C were produced as described in Example 4 for protein S and further purified. The monoclonal antibodies for protein C were coupled to CNBR-Sepharose 4B (Pharmacia). The following buffers were used for purifying the protein C by affinity chromatography:

absorption buffer: 20 mmol Tris, 2 mmol EDTA, 0.25 mol NaCl and 5 mmol benzamidine;

washing buffer: 20 mmol Tris, 1 mol NaCl, 2 mmol benzamidine, 2 mmol EDTA; the pH was 7.4;

eluting buffer: 3 mol NaSCN, 20 mmol Tris, 1 mol NaCl, 0.5 mmol benzamidine, 2 mmol EDTA.

In detail, the prothrombin complex concentrate was dissolved in the absorption buffer, about 10 g of the prothrombin complex concentrate being used for a 20 ml monoclonal antibody column. Subsequently the dissolved prothrombin complex concentrate was filtered, centrifuged at 20,000 rpm for 15 min and sterile filtered through a 0.8 μm filter. The sterile filtered and dissolved prothrombin complex concentrate was applied to the column at a flow rate of 10 ml/h. Subsequently the column was washed protein-free with the washing buffer, and finally the bound protein C was eluted with the eluting buffer at a flow rate of 5 ml/h and the fractions were collected. The eluted protein C was dialyzed against a buffer (0.2 mol/l Tris, 0.15 mol glycine and 1 mmol EDTA, pH 8.3). The protein C content was determined in terms of its antigenicity by the method of Laurell, and in terms of its activity according to Protac activation.

Activation of the purified protein C was effected by coupling 70 ml of thrombin (500 NIH units/ml, corresponding to approximately 2000 NIH units/mg of protein) to CNBR Sepharose 4B (Pharmacia), whereupon protein C was mixed with the thrombin gel at a ratio of approximately 6 units of protein C to 1 unit of thrombin at 37° C. and kept reacting with continuous shaking for 8 hrs. Thereupon the protein C activity was determined with chromogenic substrate (S 2366). Subsequently the activated protein C was sterile filtered and optionally frozen.

EXAMPLE 7

Highly purified protein C may also be prepared as described in Example 3 for protein S, by means of polyclonal affinity chromatography by producing protein C antiserum, by immunization of sheep and plasmapheresis of the animals.

According to the following working procedure, 40 mg of monoclonal purified protein C were coupled to CNBR Sepharose 4B (Pharmacia). 150 ml of the sheep anti-protein C IgG fraction were applied to the protein C column in the following buffer: 500 mmol NaCl, 20 mmol Tris, 10 mmol benzamidine, 10 mmol $CaCl_2$.

Subsequently the column was washed free from proteins with the same buffer. The calcium-dependent antibody fraction was obtained by elution with the following buffer: 100 mmol NaCl, 20 mmol Tris, 3 mmol EDTA.

Approximately 6% of all the applied sheep IgG fraction was eluted under these conditions. The calcium-dependent IgG fraction was separated from the column with 4 mol of guanidine. The calcium-dependent (metal ion-dependent) protein C antibody fraction obtained was subsequently coupled to a CNBR Sepharose 4B (Pharmacia).

Prothrombin complex concentrate was dissolved in 500 mmol NaCl, 20 mmol Tris, 10 mmol benzamidine, 20 mmol $CaCl_2$ and applied to the calcium-dependent polyclonal anti-protein C Sepharose, whereupon it was washed with the same buffer and eluted with the following buffer: 100 mmol NaCl, 20 mmol Tris, 2 mmol benzamidine, 3 mmol EDTA. Then the eluted protein C was further treated and activated in a similar manner as described for the monoclonal purified protein C according to Example 6.

Formulation of the highly purified protein C prepared according to Example 6 or 7 to a pharmaceutically administrable preparation was carried out in the same manner as described for protein S according to Example 5.

EXAMPLE 8

Thermal treatment of the antibodies directed against protein C or protein S 25 ml of an aqueous solution of a monoclonal antibody for protein C, which solution was prepared according to Example 7, were diafiltered against the 6-fold volume of an 0.75% glycine solution, whereupon 0.45 g of sorbitol were added. Then the solution was frozen and lyophilized. The lyophilisate was moistened with water to 7.6% and heated under $N_2$ atmosphere for 10 hours at 80° C. to inactivate any pathogens possibly present.

100 mg of this antibody were immobilized on 25 ml Affigel 10 (Bio-Rad), more than 99% of the protein used thus being bound. For recovering protein C, the protein C from a prothrombin complex concentrate was bound to the immobilized monoclonal antibody, as described in Example 6, and eluted. The yield was 600 μg of protein C per ml of gel.

In the same manner also, protein S could be recovered by the aid of antibodies for protein S, which antibodies had been thermally treated prior to immobilization.

EXAMPLE 9

Efficacy of activated protein C for the prevention of thromboses in the rabbit thrombosis model Activated protein C was rated as effective regarding the prevention of thromboses if the clot was graded +1 or less. Activated protein C injected in doses of from 500 to 1000 μg/kg 5 min prior to FEIBA application, was effective in 18 animals. The non-effective form had no thrombosis-preventing effect in this model.

EXAMPLE 10

In a combined application of protein S and activated protein C, 280 μg of activated protein C and 500 μg of protein S were used per kg.

Such a combination is fully effective in the thrombosis model as regards thrombosis prevention. In the combined application, the individually active substances had a thrombosis-preventing effect in markedly lower concentrations, as can be seen in Table 2. Thus, a synergistic or additive effect is to be assumed. No prolonged haemorrhages from the inflicted wounds were observed.

For the purification by means of polyclonal or monoclonal anti-protein S affinity chromatography as described, the IgG-containing substances may be thermally treated for safety reasons, i.e. at a temperature and for a time sufficient to inactivate any pathogens, in particular viruses, possibly present.

What we claim is:

1. A method of treating and preventing thromboembolic complications in patients afflicted with congenital or acquired Protein S deficiencies, the method comprising administering to the patient a therapeutic composition comprising Protein S at a concentration at least 50 times that present in native plasma and free from C4b-binding protein, wherein the protein S has been purified by either polyclonal affinity chromatography or monoclonal affinity chromatography.

2. A therapeutic composition for treating and preventing thromboses and thromboembolic complications, the composition comprising Protein S at a concentration at least 50 times that present in native plasma and being substantially free of C4b-binding protein together with a pharmaceutically acceptable carrier.

3. The composition according to claim 2 further comprising activated protein C.

4. The composition according to claim 2 wherein the Protein S has been purified by either polyclonal anti-Protein S affinity chromatography or monoclonal anti-Protein S affinity chromatography.

5. A composition comprising Protein S at a concentration at least 50 times that present in native plasma and being substantially free of C4b-binding protein.

6. The composition according to claim 5 further comprising activated protein C.

7. The composition according to claim 5 wherein the Protein S has been purified by either polyclonal anti-Protein S affinity chromatography or monoclonal anti-Protein S affinity chromatography.

* * * * *

UNITED STATES PATENT AND TRADEMARK OFFICE
CERTIFICATE OF CORRECTION

PATENT NO. : 5,254,532

DATED : October 19, 1993

INVENTOR(S) : Schwarz et al.

It is certified that error appears in the above-identified patent and that said Letters Patent is hereby corrected as shown below:

On the title page, item [73], the name of the Assignee from "Immuno Aktiengesellschaft für chemisch-medizinische Produkte" should read --IMMUNO Aktiengesellschaft--.

Signed and Sealed this

Twentieth Day of September, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,254,532

DATED : October 19, 1993

INVENTOR(S) : Schwarz et al.

It is certified that error appears in the above-identified patent and that said Letters Patent is hereby corrected as shown below:

Title page, Item 73, 3rd line, "Australia" should read --Austria--.

Column 1, line 60, "provides" should read --provides a--.

Column 1, line 65, "activates" should read --activated--;

Column 2, line 50, "by mens" should read --by means--.

Column 3, line 68, "of" should read --by--.

Column 4, line 3, "AG" should read --AG8- --.

Column 6, line 10, "8 hrs." should read --3 hrs.--.

Signed and Sealed this

First Day of October, 1996

Attest:

BRUCE LEHMAN

Attesting Officer        Commissioner of Patents and Trademarks